(12) United States Patent
Roulier et al.

(10) Patent No.: US 6,245,343 B1
(45) Date of Patent: Jun. 12, 2001

(54) SOLID FOAMING PULVERULENT COMPOSITION TO BE HYDRATED FOR CARING FOR OR CLEANING THE SKIN

(75) Inventors: Veronique Roulier, Paris; Therese Daubige, Mousseaux les Bray; Veronique Guillou, Asnieres, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/332,901

(22) Filed: Jun. 15, 1999

(30) Foreign Application Priority Data

Jun. 15, 1998 (FR) .................................................. 98 07519

(51) Int. Cl.$^7$ .............................. A61K 7/02; A61K 7/048; A61K 7/50
(52) U.S. Cl. ......................... 424/401; 510/130; 510/137; 510/138; 510/139; 510/158; 514/844; 514/975
(58) Field of Search .............................. 424/401; 510/119, 510/127, 130, 137, 138, 139, 158; 514/844, 846, 950, 951, 975

(56) References Cited

U.S. PATENT DOCUMENTS

| | | | |
|---|---|---|---|
| 5,219,561 | * 6/1993 | Gagnebien et al. | 424/69 |
| 5,593,680 | * 1/1997 | Bara et al. | 424/401 |
| 5,720,961 | * 2/1998 | Fowler et al. | 424/401 |
| 5,728,389 | * 3/1998 | Sebillotte-Arnaud | 424/400 |
| 5,753,245 | * 5/1998 | Fowler et al. | 424/401 |
| 5,763,500 | * 6/1998 | Roulier et al. | 521/84.1 |
| 5,824,296 | * 10/1998 | Dubief et al. | 424/70.11 |
| 5,888,951 | * 3/1999 | Gagnebien et al. | 510/130 |
| 5,914,117 | * 6/1999 | Lavaud | 424/401 |
| 6,024,943 | * 2/2000 | Ness et al. | 424/59 |

FOREIGN PATENT DOCUMENTS

| | | |
|---|---|---|
| 44 20 880 A1 | 12/1995 | (DE) . |
| 0 745 379 A1 | 12/1996 | (EP) . |

\* cited by examiner

*Primary Examiner*—Robert H. Harrison
(74) *Attorney, Agent, or Firm*—Oblon, Spivak, McClelland, Maier & Neustadt, P.C.

(57) ABSTRACT

The invention relates to a foaming pulverulent composition for cleaning and/or caring for the skin. The composition includes a cosmetically acceptable binder and a pulverulent filler which is insoluble in the binder and which is present in an amount sufficient to structure the composition and to confer on it the appearance of a deformable solid in which the binder is trapped. The pulverulent filler includes solid particles of thermoplastic polymer and at least one surfactant in pulverulent form. The composition foams when it is hydrated.

31 Claims, No Drawings

SOLID FOAMING PULVERULENT COMPOSITION TO BE HYDRATED FOR CARING FOR OR CLEANING THE SKIN

BACKGROUND OF THE INVENTION

1. Field of the Invention

The present invention relates to a foaming pulverulent composition, having a deformable solid appearance, for deep cleaning and/or caring for the skin. The composition can be applied both to the human face and to the human body and is very soft to the touch. The composition, is hydrated before use.

The invention also relates to a cosmetic process for cleaning and/or caring for the skin and to a process for the manufacture of the pulverulent composition.

2. Discussion of the Background

Cleaning compositions for the skin are usually provided in the form of solid bars, such as soaps, or in the form of more or less viscous liquids.

Consumers generally make use of the whole soap when cleaning themselves with soap. The soap has a tendency to soften as it is used, due to contact with water, and, as a result, the soap tends to age badly. In addition, it is often the case that the soap breaks up, and consumers find themselves with small bits of soap that are difficult to use. Furthermore, a wet soap is generally slippery, which makes it difficult to use, particularly by young children. For this reason, it is increasingly common to use liquid cleaners in place of soaps. Unfortunately, the more liquid the compositions, the more difficult they are to measure out because they have a tendency to escape between the fingers, and a greater tendency to escape from their packaging. This can be a great nuisance when the liquid compositions come into contact with clothing, for example, or when being moved.

It is also known to use cleansing masks for the deep cleaning of the face. The cleansing masks are generally provided in the form of a gel or cream, to be applied as a thin layer over the skin, and typically include powders capable of absorbing the fatty substances produced by the skin, such as sebum. These masks may optionally include a cosmetic or dermatologically active principles of the skin for cleaning the skin and/or contributing to the well being of the skin. Such masks are disclosed in particular in U.S. Pat. No. 5,690,945 and WO-A-86/05394. These masks are often heavy to wear, however, and are not very comfortable (e.g. due to their tightness), and the cleaning is not always felt to be effective. Furthermore, these masks are difficult to rinse off.

Accordingly, users are increasingly looking for novel textures and novel types of product that avoid the above-mentioned problems.

SUMMARY OF THE INVENTION

Accordingly, one object of the present invention is to provide a novel composition for cleaning and/or caring for the skin which makes it possible to overcome the disadvantages mentioned above.

Another object is to provide a foaming composition which is easy to apply, which is very light, which has great softness and which gives an effect of well being after application.

Another object is to provide a composition that has the advantage of rinsing off in an outstanding way and that exhibits an entirely unusual texture.

These and other objects are achieved by the present invention, of which the first embodiment relates to foaming pulverulent composition for cleaning and/or caring for the skin, which includes:

a cosmetically acceptable binder; and a pulverulent filler which is insoluble in the binder;

wherein the pulverulent filler includes solid particles of thermoplastic polymer and at least one surfactant in pulverulent form;

wherein the pulverulent filler is present in an amount sufficient to structure the composition and to confer on it the appearance of a deformable solid in which the binder is trapped; and wherein the composition foams when hydrated.

Another embodiment of the present invention relates to a cosmetic for cleaning and/or caring for human skin, that includes the composition above.

Another embodiment of the present invention relates to a cosmetic process for cleaning and/or caring for the skin, that includes hydrating the composition above, thereby causing it to foam, applying to the skin and rinsing the skin.

Another embodiment of the present invention relates to a process for preparing the composition above, that includes introducing the binder and then the filler into a mixer-extruder and then shaping the composition emerging from the mixer-extruder in a die of desired shape.

DESCRIPTION OF THE PREFERRED EMBODIMENTS

Other features of the invention will become apparent in the course of the following descriptions of preferred embodiments, which are given for purposes of illustration of the invention and are not intended to be limiting unless otherwise specified.

Preferably, the standard composition of the invention is intended more especially for cleaning and/or caring for the human face. It is provided in the form of a deformable or malleable dry solid which does not stain and which resembles marshmallow (see the document U.S. Pat. No. 3,682,659 for the consistency of marshmallow, the entire contents of which are hereby incorporated by reference). This solid can be modeled like children's plasticine. It can be easily broken by hand in order to remove only the necessary amount of product. In particular, this composition can be packaged in single-dose form, which is particularly advantageous from the viewpoint of hygiene, for example in the form of small cubes, of balls or of tetrahedra.

Preferably, by virtue of this solid texture, there is no risk of the composition of the invention escaping from its packaging, in particular during its transportation. Furthermore, this composition is very easy to grasp and so does not flow between the fingers; it is much simpler to measure out than standard liquid cleaners and the problem of wear of hard soaps does not exist. Furthermore, it is easy, light and pleasant to apply. Moreover, its storage does not present any problems and its contamination by the surroundings and/or the handling by the consumer is relatively reduced and in any event much less than that of the comparable products of the prior art. In particular, it is not necessary to introduce a preservative in order to provide for its antimicrobial protection.

Preferably, by virtue of the particles of the invention, it is possible in particular to obtain a homogeneous structure (deformable solid) for constituents normally resulting in two separate phases (immiscible constituents, for example oil/water).

The texturizing agent of the invention preferably exhibits the distinguishing feature of being easily removed from the skin by simple dilution. In fact, it acts as a vehicle or reservoir for the cosmetic binder. In addition, it makes it possible, when necessary, to recover the binder and in particular the active principle or principles, trapped in the deformable solid, by simple dilution with water. This is probably due to the fact that the cosmetic medium is housed in the interparticulate spaces of the solid and not in the particles.

For the purpose of obtaining a solid with a pleasant and soft touch, it is preferable to use particles having a particle size of 1 $\mu$m to 300 $\mu$m, for example of 5 $\mu$m to 200 $\mu$m and preferably of 10 $\mu$m to 100 $\mu$m and better still of 15 $\mu$m to 40 $\mu$m.

The great softness contributed by these particles makes it possible for people with sensitive skin to use the composition of the invention. By virtue of the presence of the surfactant and of the thermoplastic polymer in pulverulent form, cleaning is carried out thoroughly and very smoothly, without drying and tightening the skin.

In order to confer a light and airy appearance on the mask of the invention, use is preferably made of particles having a relative density of less than 0.09 and better still of less than 0.06 and even better still of less than 0.04.

For the purpose of obtaining this low relative density, use is advantageously made of hollow particles filled with a gas. This gas can be air, nitrogen, isobutane, isopentane, and the like.

Preferably, the particles are provided in the form of beads. However, it is possible to use particles having the form of fibres.

These particles can be prepared from different inert materials which do not react chemically with the cosmetically acceptable binder; preferably, the particles do not react with the oils, the surfactants, the water and the various other constituents of the composition, such as the active principles.

The powder of the invention, which confers the deformable solid texture, preferably has the distinguishing feature of readily disintegrating by simple dilution in a solvent, such as water optionally charged with salts or trace elements.

Preferably, as the criterion for the choice of powder, the following test can be carried out:

addition of specific particles to water comprising a dye conventionally used in the cleaning field, such as the disodium salt of Brilliant Blue FCF, listed in the Colour Index under the reference CI 42090, until a coloured paste is obtained, pouring a drop of water onto the paste.

When the paste at the point of impact of the water drop is much lighter in colour than the remainder of the paste, this means that the particles under consideration are appropriate for texturizing the composition. Conversely, when the paste at the point of impact has not lightened in colour, the particles under consideration are in no way appropriate.

The inert particles are preferably prepared from thermoplastic materials, such as polyamides, for example nylon, or polymers or copolymers of acrylonitrile, of vinylidene chloride, of vinyl chloride and/or of acrylic or styrene monomer, which are optionally expanded. The acrylic monomer is, preferably, a methyl or ethyl acrylate or methacrylate. The styrene monomer is preferably α-methylstyrene or styrene.

Use may be preferably made, as nylon particles, of the "Orgasol" particles sold by the company Atochem. Preferably these particles are porous solid spheres with a diameter ranging from 5 $\mu$m to 60 $\mu$m, more preferably from 10 $\mu$m to 50 $\mu$m, and most preferably from 15 to 45 $\mu$m.

The particles are preferably hollow deformable particles of expanded copolymer of vinylidene chloride and of acrylonitrile or of vinylidene chloride, of acrylonitrile and of methacrylate. Use may be made, for example, of a copolymer comprising: from 0% to 60% of units derived from vinylidene chloride, from 20% to 90% of units derived from acrylonitrile and from 0% to 50% of units derived from an acrylic or styrene monomer, the sum of the percentages (by weight) being equal to 100. These particles are provided in particular in the dry or hydrated state and can be obtained, for example, according to the processes disclosed in Patents and Patent Applications EP-A-56,219, EP-A-348,572, EP-A-320,473, EP-A-112,807 and U.S. Pat. No. 3,615,972, the entire contents of each of which are hereby incorporated by reference.

These hollow particles can be, for example, those formed of a terpolymer of vinylidene chloride, of acrylonitrile and of methacrylate sold under the tradename Expancel by the company Nobel Casco under the references 551 DE 12 (particle size of approximately 12 $\mu$m and density 40 kg/m$^3$), 551 DE 20 (particle size of approximately 30 $\mu$m and density 65 kg/m$^3$) or 551 DE 50 (particle size of approximately 40 $\mu$m). Mention may also be made of the microspheres formed of the same expanded terpolymer in the dry state having a particle size of approximately 18 $\mu$m and a density of approximately 60 to 80 kg/m$^3$, known hereinbelow as EL 23, or having a particle size of approximately 34 $\mu$m and a density of approximately 20 kg/m$^3$, known hereinbelow as EL 43, or having a particle size of approximately 150 $\mu$m, known hereinbelow as EL 55.

Mention may also be made, as other polymeric hollow particles which can be used in the invention, of the polymers and the copolymers obtained from itaconic, citraconic, maleic or fumaric esters or acids or from vinyl acetate or lactate (see, to this end, the document JP-A-2-112304, the entire contents of which is hereby incorporated by reference) or of the particles of non-expanded copolymer of vinylidene chloride and of acrylonitrile or of vinylidene chloride, of acrylonitrile and of methacrylate which are sold under the trade name Expancel with the reference 551 WU.

On the other hand, particles of maize starch, of pyrogenic silica, of polyethylene, of polyurethane or of polyester, which is non-expanded, do not make it possible to obtain a solid composition which is properly removed from the skin during rinsing.

Whether or not a deformable solid is obtained is related to the amount of powder or structuring agent used in the mask; above a certain amount of particles, known as critical pigment volume concentration (CPVC), a sudden increase in the viscosity of the medium is noticed. The CPVC depends on the medium and on the nature of the particles; it therefore has to be determined each time. Its determination does not present any problems for a person skilled in the art. It is possible, for example, to use the official ASTM method to determine the CPVC.

Preferably, the structuring pulverulent filler represents up to 80% by volume of the composition, of which advantageously 60% represents particles having a relative density of less than 1. Under these conditions, the binder represents up to 20% so by volume of the composition. Preferably, the particles with a relative density of less than 1 represent from 2 to 20% and better still from 3 to 7% of the total weight of the composition.

The composition of the invention may preferably include, in addition to the polymer particles, a surfactant in pulverulent form in an effective amount during the hydration of the composition. This type of agent preferably exhibits the distinguishing feature of reacting chemically with water and the structuring agent to form a foam which can be easily applied to the skin.

The composition according to the invention can preferably contain one or more cleaning and/or foaming surfactants in pulverulent form which can be non-ionic, anionic, cationic and/or amphoteric surfactants. Preferably, they can be used in an amount ranging, for example, from 10% to 80% of the total weight of the composition and preferably from 30% to 60%.

The surfactant or surfactants in the powder form preferably exhibit a particle size ranging from 5 to 50 μm and better still from 10 to 20 μm.

The composition of the invention can preferably contain in addition, one or more liquid surfactants which can represent from 20 to 88% of the total weight of the composition and better still from 33 to 67%. These liquid surfactants form part of the binder and can even constitute the binder in its entirety.

Mention may be made, as non-ionic surfactants which can be used in the invention, of, for example, the condensates of alkylene oxides and of alkylphenols, such as ethoxylated octylphenol, for example that sold under the name Triton X45 by the company Rohm and Haas, provided in anhydrous pulverulent form, the condensates of ethylene oxide, of propylene oxide and of ethylenediamine, alkylpolyglucosides, or ethers of fatty alcohols and polyols, such as, for example, Polyglyceryl-3 hydroxylauryl ether (CTFA name), sold under the name Chimexane NF by the Company Chimex.

Mention may be made, as anionic surfactants, of, for example, polyalkylene glycols ether of fatty alcohols, taurates, acyl lactylates, such as sodium stearyl lactylate (for example Pationic SSL, a pulverulent surfactant sold by Maprecos), alkyl sulphates, such as sodium lauryl sulphate (Sipon LCS, a pulverulent surfactant sold by the company Henkel), polyoxyethylenated alkyl sulphates, such as (lacuna), alkyl ether sulphates, such as monoethanolamine lauryl ether sulphate, in particular that sold at 28% in water by the company Henkel (Sipon LEM 235), alkyl ether carboxylates, monoalkyl or dialkyl phosphates, such as the mono (2-hexyldecyl) phosphate of argine (C6C10 MAP-1-ARG, a powder sold by the company Kao Chemicals), ethoxylated alkyl phosphates, N-acyl sarcosinates, such as sodium lauryl sarcosinate (for example Oramix L30, sold by the company Seppic) or sodium myristoyl sarcosinate (for example Nikkol Sarcosinate MN, a powder sold by the company Nikko), N-acyl glutamates, such as sodium lauroyl glutamate (for example Amisoft LS11, a powder sold by the company Ajinomoto), acyl isethionates, such as sodium cocoyl isethionate (sold in particular by the company Rhône-Poulenc (Gerapon AC78) or that sold as a powder by the company Jordan (Jordapon CI)), polysorbates, succinamates, soaps, such as potassium laurate, myristate, palmitate or stearate, or their mixtures.

Mention may be made, as amphoteric or zwitterionic surfactants, of, for example, betaines and betaine derivatives, sultaines and sultaine derivatives or imidazolinium derivatives, such as disodium cocoamphodiacetate (Miranol C2M concentrate, sold by the company Rhône-Poulenc).

Mention may be made, as cationic surfactants which can be used in the invention, of pyrrolidone carboxylate derivatives, such as PCA ethyl cocoyl arginate (Cation CAE, a powder sold by the company Ajinomoto).

In addition, the composition according to the invention can preferably contain oils which can be used in an amount ranging from 0% to 30% by weight and preferably from 0% to 10% of the total weight of the composition.

Preferably, the oils form an integral part of the binder.

Preferably, the oils which can be used in the compositions according to the invention can be chosen from mineral oils, such as liquid paraffin and liquid petrolatum, oils of animal origin, such as perhydrosqualene; oils of vegetable origin, such as sweet almond oil, avocado oil, castor oil, olive oil, jojoba oil, sesame oil, groundnut oil, grape seed oil, rapeseed oil, coconut oil, hazelnut oil, palm oil, apricot kernel oil, calophyllum oil, rice bran oil, maize germ oil, wheat germ oil, soybean oil, sunflower oil, safflower oil, passion flower oil, rye oil and karite butter and its liquid fraction; synthetic oils, such as fatty esters, for example butyl or isopropyl myristate, hexadecyl, isopropyl, octyl or isodecyl stearate, decyl oleate, hexyl laurate, propylene glycol dicaprylate, esters derived from lanolin acid, such as isopropyl lanolate and isocetyl lanolate, isoparaffins, acetylglycerides, octanoates of alcohols and of polyalcohols, such as those of glycol and glycerol, ricinoleates of alcohols and of polyalcohols, or fatty acid triglycerides; silicone oils, such as cyclomethicones or polydimethylsiloxanes, which are volatile and/or non-volatile, or phenyldimethylsiloxanes; or their mixtures.

In addition, the composition can preferably contain one or more other ingredients conventionally used in cleaning and/or care compositions. These ingredients are screening agents, fragrances, preservatives, antioxidants, pH-regulating agents, sequestering agents, fillers, dyes, or cosmetic or dermatological active principles. These adjuvants are used in the usual proportions for cleaning compositions, for example from 0.01 to 10% of the total weight of the composition. These adjuvants must be of such a nature and used in such an amount that they do not disturb the properties desired for the composition of the invention.

Mention may be made, as preferable active principles which can be used in the invention, of antibacterials, such as octopirox and triclosan, keratolytic agents, such as salicylic acid, essential oils or vitamins.

The composition according to the invention can be prepared by any means known to a person skilled in the art and in particular by simple mixing of the various constituents and moulding in an appropriate mould. However, it is advantageously prepared by mixing, followed by kneading and then by extrusion in an extruder, preferably a twin-screw extruder, such as those disclosed in the documents EP-A-605,284 and FR-A-2,715,306, the entire contents of each of which are hereby incorporated by reference, in which the two screws rotate in the same direction. Use may also be made of the process disclosed in the document EP-A-651,991, the entire contents of which are hereby incorporated by reference.

The various constituents of the composition are introduced at room temperature, preferably at approximately 20° C., at the inlet of the twin-screw extruder in the feed region. Preferably, the solid constituents are introduced at the head of the extruder and then the liquid constituents are introduced laterally. The combined mixture is kneaded in various regions of the extruder, which are maintained at a temperature preferably ranging from 15 to 25° C.; the mass obtained is transported towards the outlet of the extruder and extruded through a die. The rotational speed of the screws is of the order of 400 to 1000 revolutions/minute, preferably of between 550 and 650 revolutions/minute.

The extruded mass exits from the die in the form of sausages, with a diameter given according to the die used, which can subsequently be cut up and shaped, in particular in the form of a solid bar or stick. Other forms can, of course, be prepared by choosing appropriate dies and devices for shaping the final products which are suited to the desired form.

Preferably, the process for the manufacture of the pulverulent composition of the invention includes introducing the binder and then the filler into a mixer-extruder under cold conditions, mixing and extruding, and then shaping the composition emerging from the mixer-extruder in a die of desired shape.

Preferably, the extruded mass can also be dehydrated and/or milled and/or compacted. Dehydration is especially preferable when the ingredients of the composition are introduced in the form of a solution or dispersion in aqueous medium.

Since the entire extrusion process is carried out at room temperature, of the order of 20–25° C., it is possible to use heat-sensitive ingredients of the vitamin or volatile oil type.

Furthermore, the heat-sensitive ingredients can be introduced in any region of the extruder (at the head, in the middle or at the end), since no decomposition due to heat is to be feared. This is particularly advantageous for the introduction of structuring agents of the Expancel type.

It is also possible to carry out part of the extrusion under an inert gas (for example, nitrogen).

EXAMPLES

The examples below are given by way of illustration and without limitation for the purpose of more fully bringing out the characteristics of the invention. The amounts are given as % by weight.

Example 1

Pulverulent Foaming Mask for Greasy Skin with a Tendency Towards Acne

| | |
|---|---|
| Sodium cocoyl isethionate (Jordapon CI, sold by the company Jordan) (anionic surfactant is pulverulent form) | 42.5% |
| Monethanolamine lauryl ether sulphate, sold at 28% in water by the company Henkel (Sipon LEM 235) | 51.0% |
| Preservative | q.s. |
| Octopirox | 0.1% |
| Fragrance | q.s. |
| Salicylic acid | 0.5% |
| Expancel 551 DE 20 | 5.5% |

The procedure includes introducing, under cold conditions, the surfactants at the extruder head and in then introducing laterally, in the various stages of the twin-screw extruder, the active principles, the preservatives, the fragrance and, at the end, the Expancel. The mixture is extruded under cold conditions until a homogeneous paste is obtained, which paste is subsequently shaped in an appropriate die in order to produce a sausage which is cut up into sticks.

The mask obtained is a white non-sticky paste which can be easily modelled, which can be easily wetted or hydrated, which is easy to apply and remove, which is soft to the touch and which has a good foaming power.

This mask can then be hydrated and then kneaded until it foams, in particular in the hollow of the hand. The foam obtained is then applied as a thin layer to the skin of the face. The amount of water can represent from 6 to 10 times by volume that of the sample taken for the cleaning.

The impurities are released from the time of the application of the foam to the face. The anti-acne active principles subsequently penetrate into the skin in order to clean it in depth and to disinfect it for the purpose of preventing the formation of spots. The mask is removed simply with water.

Example 2

Foaming Mask for Any Skin Type

| | |
|---|---|
| Sodium cocoyl isethionate (Jordapon CI, sold by the company Jordan) (anionic surfactant in pulverulent form) | 40.0% |
| Expancel 551 DE 20 | 6.0% |
| Monoethanolamine lauryl ether sulphate, sold at 28% in water by the company Henkel (Sipon LEM 235) | 54.0% |

The procedure is the same as for Example 1 and a paste is obtained which has analogous properties.

Example 3

Foaming Mask for Sensitive Skin

| | |
|---|---|
| Sodium cocoyl isethionate (Jordapon CI, sold by the company Jordan) (anionic surfactant in pulverulent form) | 35.0% |
| Monethanolamine lauryl ether sulphate, sold at 28% in water by the company Henkel (Sipon LEM 235) | 60.0% |
| Sweet almond oil | 1.0% |
| Microspheres EL 23 | 5.0% |

The procedure is the same as for Example 1 and a paste is obtained which has analogous properties.

Obviously, numerous modifications and variations of the present invention are possible in light of the above teachings. It is therefore to be understood that within the scope of the appended claims, the invention may be practiced otherwise than as specifically described herein.

This application is based on French Patent Application FR 9807519, filed Jun. 15, 1998, the entire contents of which are hereby incorporated by reference.

What is claimed is:

1. A foaming pulverulent composition for cleaning and/or caring for the skin, which comprises:
    a cosmetically acceptable binder; and
    a pulverulent filler which is insoluble in said binder, wherein the pulverulent filler comprises solid particles of thermoplastic polymer and at least one surfactant in pulverulent form; and
    wherein the pulverulent filler is present in an amount sufficient to structure the said composition and to confer on it the appearance of a deformable solid in which the binder is trapped,
    and wherein the composition foams when hydrated.
2. The composition according to claim 1, wherein the polymer particles have a particle size of 1 µm to 300 µm.
3. The composition according to claim 1, wherein the polymer particles have a particle size of 10 µm to 100 µm.
4. The composition according to claim 1, wherein the polymer particles have a relative density of less than 0.09.
5. The composition according to claim 1, wherein the polymer particles have a relative density of less than 0.04.

6. The composition according to claim 1, wherein the filler is present at a concentration at least equal to the critical pigment volume concentration.

7. The composition according to claim 1, wherein the polymer particles are hollow.

8. The composition according to claim 1, wherein the polymer particles are selected from the group consisting of polymers and copolymers of vinylidene chloride, vinyl chloride, acrylonitrile, acrylic, and styrene, and mixtures thereof.

9. The composition according to claim 1, wherein the polymer particles are hollow particles selected from the group consisting of polymers and copolymers of vinylidene chloride copolymer, acrylonitrile copolymer, acrylic monomer and styrene monomer.

10. The composition according to claim 1, wherein the binder further comprises at least one foaming and/or cleaning liquid surfactant.

11. The composition according to claim 10, wherein the liquid surfactant is monoethanolamine lauryl ether sulphate.

12. The composition according to claim 10, wherein the liquid surfactant is present in an amount ranging from 20 to 88% of the total weight of the composition.

13. The composition according to claim 1, wherein the surfactant in pulverulent form is present in an amount ranging from 10 to 80% of the total weight of the composition.

14. The composition according to claim 1, wherein the surfactant in pulverulent form is present in an amount ranging from 30 to 60% of the total weight of the composition.

15. The composition according to claim 1, wherein the surfactant in pulverulent form is sodium cocoyl isethionate.

16. The composition according to claim 10, wherein the liquid surfactant is present in an amount 33% to 67% of the total weight of the composition.

17. The composition according to claim 1, further comprising at least one ingredient selected from the group consisting of screening agents, fragrances, preservatives, antioxidants, pH regulating agents, sequestering agents, fillers, dyes, and cosmetic or dermatological active principles, and mixtures thereof.

18. A cosmetic for cleaning and/or caring for human skin, comprising the composition according to claim 1.

19. A cosmetic process for cleaning and/or caring for the skin, comprising hydrating the composition as claimed in claim 1, thereby causing it to foam, applying to the skin, and rinsing the skin.

20. A process for preparing the composition as claimed in claim 1, comprising introducing the binder and then the filler into a mixer-extruder, mixing and extruding, and then shaping the composition emerging from the mixer-extruder in a die of desired shape.

21. The composition according to claim 1, wherein said surfactant in pulverulent form comprises one or more surfactants selected from the group consisting of non-ionic, anionic, cationic and amphoteric surfactants.

22. The composition according to claim 1, wherein said surfactant in pulverulent form comprises one or more surfactant particles having a particle size ranging from 5 to 50 $\mu$m.

23. The composition according to claim 1, wherein said surfactant in pulverulent form comprises one or more surfactant particles having a particle size ranging from 10 to 20 $\mu$m.

24. The composition according to claim 1, wherein said surfactant in pulverulent form comprises one or more non-ionic surfactants selected from the group consisting of condensate of alkylene oxide and alkyl phenol, ethoxylated octylphenol, condensate of ethylene oxide, propylene oxide and ethylenediamine, alkylpolyglucoside, and ether of fatty alcohol and polyol.

25. The composition according to claim 1, wherein said surfactant in pulverulent form comprises one or more anionic surfactants selected from the group consisting of polyalkylene glycol ether of fatty alcohol, taurate, acyl lactylate, sodium stearyl lactylate, alkyl sulfate, sodium lauryl sulfate, polyoxyethylenated alkyl sulfates, alkyl ether sulfate, monoethanolamine lauryl ether sulfate, alkyl ether carboxylate, monoalkyl phosphate, dialkyl phosphate, mono (2-hexyldecyl) phosphate of argine, ethoxylated alkyl phosphate, N-acyl sarcosinate, sodium lauryl sarcosinate, sodium myristoyl sarcosinate, N-acylglutamate, sodium lauroyl glutamate, acyl isethionate, sodium cocoyl isethionate, polysorbate, succinamate, potassium laurate, potassium myristate, potassium palmitate, potassium stearate, and mixtures thereof.

26. The composition according to claim 1, wherein said surfactant in pulverulent form comprises one or more amphoteric or zwitterionic surfactants selected from the group consisting of betaine, betaine derivatives, sultaine, sultaine derivatives, imidazolinium derivatives, disodium cocoamphodiacetate, and mixtures thereof.

27. The composition according to claim 1, wherein said surfactant in pulverulent form comprises one or more cationic surfactants selected from the group consisting of pyrrolidone carboxylate derivatives, PCA ethyl cocoyl arginate, and mixtures thereof.

28. The composition according to claim 1, wherein said composition is obtained by extrusion at a temperature ranging from 15 to 25° C.

29. The composition according to claim 1, wherein the composition is obtained by extrusion at a temperature ranging from 20 to 25° C.

30. The composition according to claim 1, wherein when said composition is hydrated, said surfactant in pulverulent form reacts chemically with water and said thermoplastic polymer to form a foam.

31. The composition according to claim 1, which is in dehydrated form.

* * * * *